US006673559B1

United States Patent
Tsarfaty et al.

(10) Patent No.: US 6,673,559 B1
(45) Date of Patent: *Jan. 6, 2004

(54) MET PROTO-ONCOGENE AND A METHOD FOR PREDICTING BREAST CANCER PROGRESSION

(75) Inventors: Ilan Tsarfaty, Frederick, MD (US); James H. Resau, Ellicot City, MD (US); Iafa Keydar, Tel Aviv (IL); Donna Faletto, Mt. Airy, MD (US); George F. Vande Woude, Berryville, VA (US)

(73) Assignee: The Government of the United States of America as represented by the Department of Health and Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 07/903,588

(22) Filed: Jun. 26, 1992

Related U.S. Application Data

(63) Continuation-in-part of application No. 07/642,971, filed on Jan. 18, 1991, now Pat. No. 5,648,273, which is a continuation-in-part of application No. 07/582,063, filed on Sep. 14, 1990, now abandoned, and a continuation-in-part of application No. 07/457,556, filed on Dec. 27, 1989, now abandoned.

(51) Int. Cl.$^7$ .................... G01N 33/574; G01N 33/567; G01N 33/53; C07K 16/00

(52) U.S. Cl. .................... 435/7.23; 435/7.1; 435/7.2; 435/7.21; 435/6; 530/388.22; 530/388.24

(58) Field of Search .................... 435/6, 7.2, 7.23, 435/7.21, 7.92, 7.93, 7.94, 7.95, 240.26; 436/501, 503; 530/388.22, 388.24

(56) References Cited

FOREIGN PATENT DOCUMENTS

| WO | WO 89/10412 | 11/1989 |
|---|---|---|
| WO | WO 91/09974 | 7/1991 |

OTHER PUBLICATIONS

Park et al. (1987), PNAS 84:6379–6383.*
Bieche et al (1992, Jan.), The Lancet 339:139–143.*
Tsarfaty et al (1992, Aug.), Science 257:1258–1261.*
C.S. Cooper, "The Met Oncogene: From Detection by Transfection to Transmembrane Receptor for Hepatocyte Growth Factor", *Oncogene* 7: 3–7 (1992).
M. Prat et al, "The Receptor Encoded by the Human c–met Oncogene is Expressed in Hepatocytes, Epithelial Cells and Solid Tumors", *Int. J. Cancer* 49: 323–328 (1991).
Montesano, et al., "Identification of a Fibroblast–Derived Epithelial Morphogen as Hepatocyte Growth Factor," *Cell*, vol. 67, Nov. 29, 1991, pp. 901–908.
G. F. Vande Woude, "Hepatocyte Growth Factor: Mitogen, Motogen, and Morphogen," *Jap. J. Can. Res.* 83: (1992).

* cited by examiner

*Primary Examiner*—Yvonne Eyler
(74) *Attorney, Agent, or Firm*—Needle & Rosenberg, P.C.

(57) ABSTRACT

A method for predicting breast tumor metastasis entails determining the amount of met protein in tumor tissue relative to normal breast duct tissue.

4 Claims, 9 Drawing Sheets

FIG. 1A
FIG. 1B
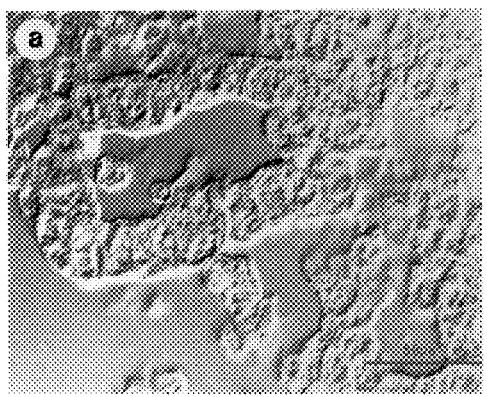
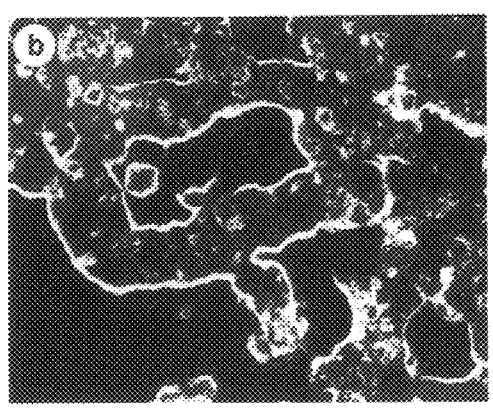

FIG. 3A
FIG. 3B
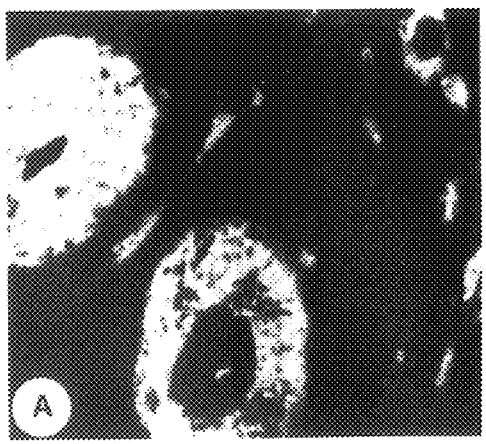
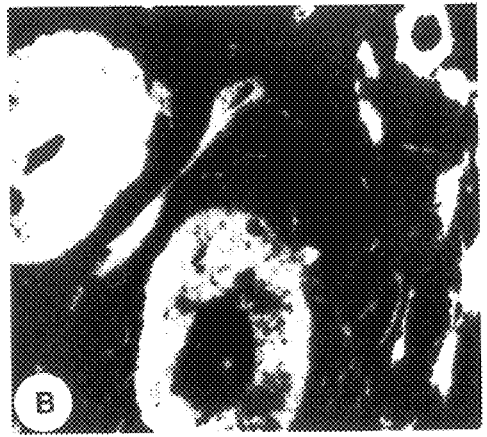

FIG. 3C
FIG. 3D
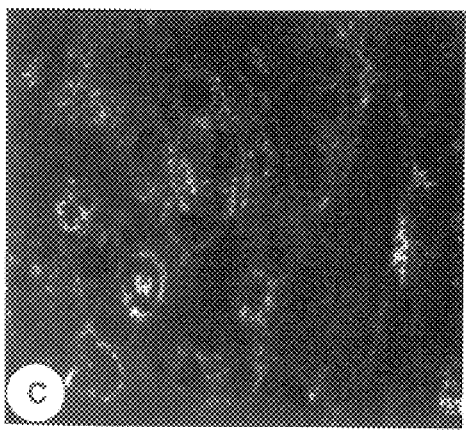
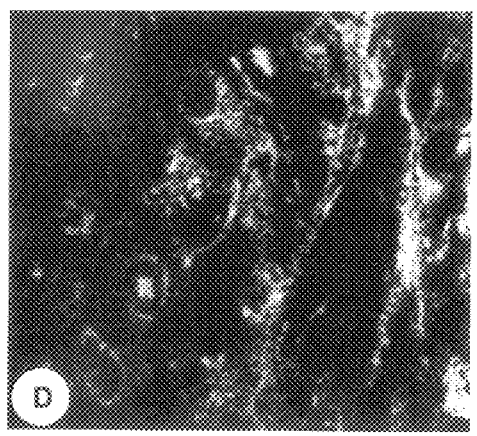

FIG. 4A
FIG. 4B
FIG. 4C
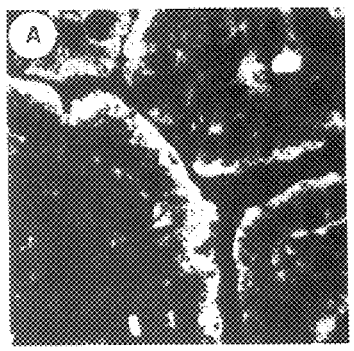
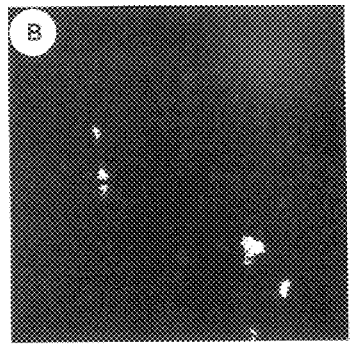
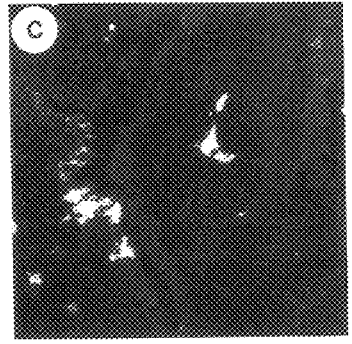

FIG. 4D
FIG. 4E
FIG. 4F
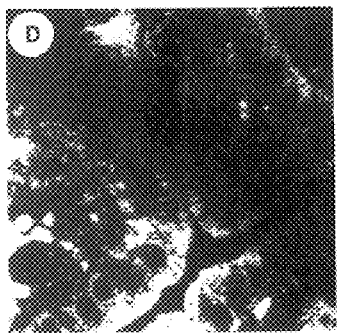
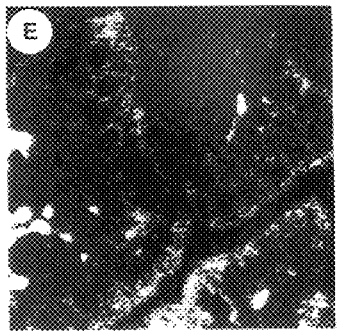
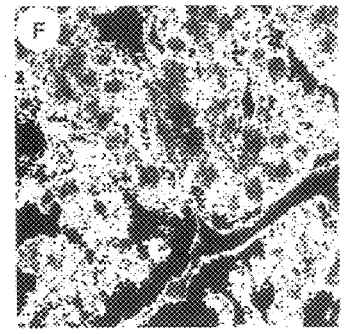

MET PROTO-ONCOGENE AND A METHOD FOR PREDICTING BREAST CANCER PROGRESSION

This is a continuation-in-part of application Ser. No. 07/642,971, filed Jan. 18, 1991, now U.S. Pat. No. 5,648,273 which is a continuation-in-part of application Ser. No. 07/457,556 filed Dec. 27, 1989 now abandoned, and application Ser. No. 07/582,063 filed Sep. 14, 1990 now abandoned. The entire contents of these applications are hereby incorporated by reference.

BACKGROUND OF THE INVENTION

The human met protooncogene product (Met or Met protein) a member of the family of tyrosine kinase growth factor receptors, was identified via the activated oncogene tpr-met (C. S. Cooper et al., *Nature* 311: 29 (1984); M. Park et al., *Cell* 45: 895 (1986)). Met is synthesized as a glycosylated 170-kD precursor and cleaved in the external (ligand binding) domain to yield a mature disulfide-linked α- (50-kD), β- (140-kD) heterodimer (C. S. Cooper et al., *Nature* 311: 29 (1984); S. Girodano et al., *Oncogene* 4: 1383 (1989); D. L. Faletto et al., *Oncogene,* in press (1992)). The Met receptor is expressed in a wide variety of tissue and cell types, but the highest levels are found in epithelial cells (M. F. Di Renzo et al., *Oncogene* 6: 1997–2003 (1991); A. Iyer et al., *Cell Growth & Diff.* 1: 87 (1990)).

Hepatocyte growth factor (HGF) was first purified from human and rabbit plasma and rat platelets on the basis of its ability to stimulate mitogenesis of rat hepatocytes (E. Gohoda et al., *J. Clin. Invest.* 81: 414 (1988); R. Zarnegar and G. Michalopoulos, *Cancer Res.* 49: 3314 (1989); T. Nakamura et al. *FEBS Lett.* 224: 311 (1987)). Thus, HGF may act as a humoral factor promoting liver regeneration after partial hepatectomy or liver injury (G. K. Michalopoulos, *FASEB J.* 4: 176 (1990)). The same factor was purified from human fibroblast culture medium and shown to act on melanocytes and a variety of epithelial and endothelial cells (J. S. Rubin et al., *Proc. Natl. Acad. Sci. U.S.A.* 88: 415 (1990)). Together with evidence of HGF expression in several organs (J. S. Rubin et al., *Proc. Natl. Acad. Sci. U.S.A.* 88: 415 (1990); K. Tashiro et al. *Proc. Natl. Acad. Sci. U.S.A.* 87: 3200 (1990); R. Zarnegar et al., *Proc. Natl. Acad. Sci. U.S.A.* 87: 1252 (1990); T. Kinoshita et al. *Biochem. Biophys. Res. Comm.* 165: 1229 (1989)), these findings indicate that HGF may also act as a paracrine mediator of proliferation for a broad spectrum of cell types. Molecular cloning of HGF revealed a remarkable structural homology to plasminogen and related serine proteases (J. S. Rubin et al., *Proc. Natl. Acad. Sci. U.S.A.* 415 (1990); T. Nakamura et al., *Nature* 342: 440 (1989); K. Miyazawa et al., *Biophys. Res. Comm.* 163: 967 (1989)).

HGF is structurally related to the family of serine proteases that includes plasminogen, prothrombin, urokinase, and tissue plasminogen activator (J. S. Rubin et al., *Proc. Natl. Acad. Sci. U.S.A.* 88: 415 (1990)); T. Nakamura et al., *Nature* 342: 440 (1989)). As defined in the present invention, HGF includes a variant of HGF previously characterized as a broad-spectrum mitogen called plasminogen like growth factor (PLGF). Several proteases, including members of the serine protease family, stimulate DNA synthesis presumably through a proteolytic mechanism similar to tryptic activation of the insulin receptor (S. E. Shoelson et al. *J. Biol. Chem.* 263: 4852 (1988)). Only urokinase has been found to associate with a specific cell-surface receptor, which itself bears no homology to any known tyrosine kinase receptors (A. L. Roldan et al., *EMBO J.* 9: 467 (1990)).

U.S. patent application Ser. No. 07/642,971, incorporated by reference above, describes the complex comprising HGF and met protooncogene protein and identifies the met protooncogene as the receptor for HGF.

Scatter factor (SF) originally had been considered to be related to but different from HGF, SF being associated with cell motogenicity (motility), and HGF being associated with cell mitogenicity (growth). However, recently it has been shown that HGF is identical to SF, and this factor is now referred to as "HGF/SF" (E. Gerardi et al., *Cancer Cells* 3: 227 (1991); E. M. Rosen et al., *Cell Growth & Diff.* 2: 603 (1991); L. Naldini et al., *EMBO J.* 10: 2876 (1991b); K. M. Weidner et al., *Proc. Natl. Acad. Sci. USA* 88: 7001 (1991)) and has been independently shown both to promote epithelial cell motility (scattering) and to cause certain epithelial cell lines to become invasive in in vitro assays (E. M. Rosen et al., *Cell Growth & Diff.* 2: 603 (1991); M. Stoker et al., *Nature* 327: 239 (1987)).

The scattering response of HGF/SF establishes that this factor is responsible for cell motility and differentiation (G. F. Vandewoude Japan. *J. Can. Res.* 83: cover (1992)). For instance, MDCK cells grown in collagen gels in the presence of HGF/SF form bracing tubules, suggesting that the three-dimensional geometry of cell-substrate interactions directs MDCK cells to organize into tubules in response to HGF/SF (R. Montesano et al., *Cell* 67: 901 (1991)).

It is known that mammary gland epithelia undergo developmental changes during pregnancy to become secretory. In culture, mammary epithelial cells can regain their differentiated phenotype only when appropriate hormonal and substratum conditions are provided (M. J. Bissell et al., *The Mammary Gland,* M. Neville and C. Daniel, Eds. (Plenum Press Publishing Corp., New York, pp. 97–146 (1987); C. H. Streuli et al., *J. Cell Biol.* 115: 1383 (1991)). Thus, a need exists to determine whether there is met expression in normal breast duct cells and to determine the role that HGF/SF and met play in the differentiation of ductal epithelium in the mammary gland. In this connection, a need also exists to determine whether there is a general phenotype in epithelial cancers arising from organs that normally involve met expression for differentiation.

The work of Bieche et al., *The Lancet,* 339: 139 (1992) has shown that the loss of heterozygosity on chromosome 7q is associated with aggressive primary breast cancer. Specifically, Bieche et al. used the c-met proto-oncogene probe, which detects sequences on chromosome 7q31, to analyse tumor and blood leucocyte DNA samples from 245 patients with primary breast cancers. The pmet H polymorphic probe detected a high frequency of allele loss (40–50%) among the 121 informative (heterozygous) patients. This genetic alteration was not significantly associated with standard prognostic features including tumor size, histopathologic grade, and lymph-node or steroid receptor status. However, patients with loss of heterozygosity on chromosome 7q31 in primary tumor DNA had significantly shorter metastasis-free survival and overall survival after surgery than patients without this alteration. Based upon this observation, Bieche et al. hypothesized that the region on chromosome 7 detected by the probe might be the site of a breast cancer or metastasis suppressor gene. Bieche et al. did not identify a specific genetic locus responsible for poor prognosis in breast cancer patients.

Thus, one object of the present invention is to provide a method for predicting the progression of breast cancer based upon the presence of Met, met DNA and met mRNA in normal and breast cancer tissue. Such a method would be advantageous in the management of breast cancer therapy, used either alone or in conjunction with other prognostic features such as tumor size, histo- and cytopathological grade and lymph node or steroid receptor status.

SUMMARY OF THE INVENTION

The present invention relates to a method for predicting breast tumor progression by determining one or more of met DNA abundance, met mRNA abundance, or Met protein abundance in normal breast tissue, wherein a higher abundance of met genes, met mRNA, or Met protein in the normal tissue than in the tumor tissue indicates a high likelihood of tumor metastisis.

BRIEF DESCRIPTION OF THE DRAWINGS

FIGS. 1A and 1B are ×2.45 magnification of the lower right hand portion of FIGS. 1A and 1B. Overall magnification is ×490.

FIG. 1C specifically shows the fluorescence in the apical region of the lumen for the right lumen.

FIG. 1D specifically shows the fluorescence in the apical region of the lumen for the upper left lumen.

FIG. 1E specifically shows the fluorescence in the apical region of the lumen for an area adjacent to the upper left lumen.

FIG. 3 expression of Met in breast tissue biopsies. A paraffin-embedded section of biopsy from breast adenocarcinoma was subjected to indirect immunofluorescence staining with c28 antibody or monoclonal antibody 4G10. The cells and immunofluorescence were analyzed by CLSM.

FIG. 3A shows immunofluorescence of normal mammary duct, performed with C28. Magnification ×250.

FIG. 3B shows immunofluorescence of normal mammary duct, performed with anti-P-Tyr. Magnification ×250.

FIG. 3C shows immunofluorescence of normal mammary duct, performed with C28. Magnification ×250.

FIG. 3B shows immunofluorescence of normal mammary duct, performed with anti-P-Tyr. Magnification ×250.

FIGS. 4A–F relate to expression of Met in the mouse embryonal digestive tract. Eleven-day-old BALB/c mouse embryos were fixed, embedded in paraffin, and subjected to immunofluorescence staining with SP260 and 4G10 antibodies. Magnification is ×220.

FIG. 4A shows apical staining of the lumen of the digestive tract with SP260.

FIG. 4B shows staining in the absence of the primary SP260 antibody.

FIG. 4C shows staining in the presence of SP260 competing peptide.

FIG. 4D shows apical staining of the lumen of the digestive tract with SP260.

FIG. 4E shows immunofluorescence with 4G10.

FIG. 4F shows an analysis of the overlap between the Met and the anti-P-Tyr staining by a confocal image processing program.

FIG. 5A shows SW480 cells grown for 18 hours in complete medium without HGF/SF.

FIG. 5B shows SW480 cells grown for 18 hours in complete medium with HGF/SF at 1 ng/ml.

FIG. 5C shows SW480 cells grown for 18 hours in complete medium with HGF/SF at 5 ng/ml.

FIG. 5D shows SW480 cells grown for 18 hours in complete medium with HGF/SF at 10 ng/ml.

FIG. 5E shows SW480 cells grown for 18 hours in complete medium with HGF/SF at 100 ng/ml.

DETAILED DESCRIPTION OF THE INVENTION

Figure 1C:
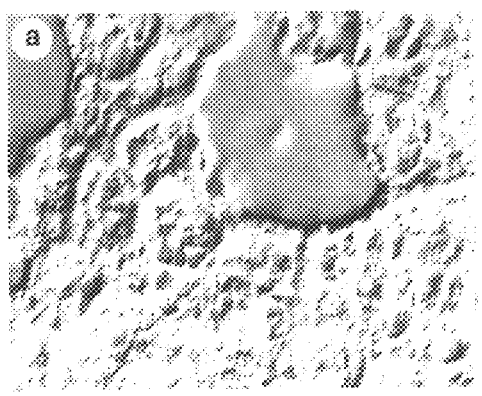
FIGS. 1c through 1E show quantitative determination of the Met-specific immunofluorescence. The histograms show the distribution of fluorescence of the bracketed areas.
Figure 1D:
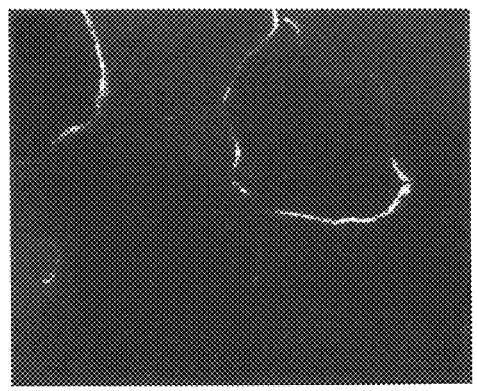
Figure 1E:
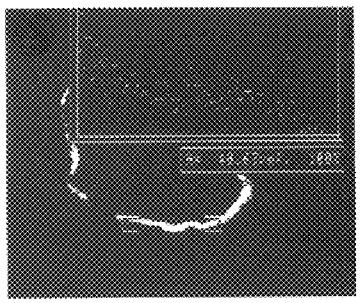
Figure 1F:
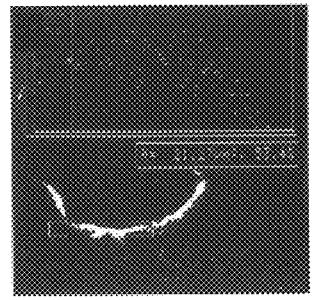
FIG. 1 shows the expression of Met in cells bordering lumen-like structures of the breast cancer cell line T47D. T47D cells were treated with Bouin's fixative, embedded in paraffin, serial sectioned, and stained by indirect immunofluorescence. Cells were analyzed using confocal laser scanning microscopy (CLSM).
FIG. 1A shows a Nomarski image of the lumen-like structures in T47D cells in culture.
FIG. 1B shows immunofluorescent staining of the same region as in FIG. 1A with Met C28 antibody.
Figure 1G:
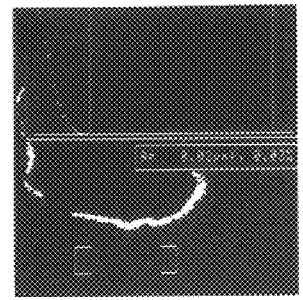

It has been discovered that Met protein and RNA products are prognostic in evaluating tumor progression towards metastasis in human breast cancer. More specifically, expression of the met protooncogene product in normal tissues has been found to be associated with the formation of highly ordered, fully differentiated lumen structures and that the ligand for Met, HGF, plays a key role in inducing the formation of these structures. It also has been discovered that, while met expression is very high in cells that form normal breast ducts, expression of met in adjacent, poorly differentiated cancer tissue is markedly reduced. This information has led to the further discovery that reduced met expression correlates with poor prognosis in human breast cancer.

The method of the present invention involves comparing the relative amounts of Met, met DNA or met mRNA in normal breast tissue and in tumor tissue. This is accomplished by determining one or more of met DNA abundance, met mRNA abundance, or Met protein abundance in normal breast tissue and breast tumor tissue from the same patient. The detection of a higher abundance of met DNA, met mRNA or Met protein in normal tissue than in tumor tissue is indicative of a poor prognosis.

In one embodiment of the present invention, the method involves contacting a sample of breast tissue containing both normal and tumor cells with an antibody reagent specific for Met protein, under antibody binding conditions. Greater binding of the reagent to normal than to tumor tissue indicates a poor prognosis. The term "normal tissue" is intended to include non-tumor tissue, but particularly lumen-forming tissue such as breast duct tissue.

Preferably, the breast tissue sample is a "section," i.e., a histological section obtained from a surgical or biopsy procedure, according to techniques well known in the art. The term "contacting" is intended to encompass any technique which permits the antibody reagent to bind with Met protein.

By "antibody reagents" is meant whole antibodies and parts thereof, either alone or conjugated with other moieties. Antibodies include polyclonal antibodies, monoclonal antibodies, and single chain antibodies. Antibody fragments are those the bind the Met protein, including Fab and $F(ab)_2$ fragments, inter alia. The antibody reagents may comprise antibodies made in animals or by recombinant DNA techniques. Also the antibody reagents include antibody and antibody fragments conjugated to, among other moieties, detectable labels, such as enzymatic labels and fluorescent labels. Radionuclides are among other useful labels which can be comprised of the antibody reagents.

Antibody binding conditions generally are well known in the art and, for the most part, will include neutral pH, moderate salt, temperatures between 2–3° C. and 37° C., incubation times between several minutes and overnight or longer. Preferred conditions include those described by M. Gonzatti-Haces et al., *Proc. Natl. Acad. Sci. USA* 85: 21 (1988) for a rabbit antibody prepared against the extracellular domain of the Met peptide, those of M. Park et al., *Proc. Natl. Acad. Sci. USA* 84: 6379 (1987) for a rabbit anti-mouse Met and the conditions described by D. K. Morrison et al. *Cell* 58: 649 (1989)) for a mouse monoclonal antibody to phosphorylated tyrosine (P-Tyr). It will be readily appreciated by those of ordinary skill in the art that the details of an antibody binding procedure may be adjusted to favor improved signal to noise ratios or sensitivity, rapidity or completeness, and the like. Moreover, conditions may be adjusted to accommodate different histological procedures for fixation and staining. Finally, it will be appreciated that titers and appropriate dilutions will be different for different antibody reagent preparations.

Binding of the antibody reagent with Met protein may be determined by any method known to the skilled artisan and may include visualization by conventional or confocal laser scanning microscopy.

The term "greater binding" is readily understood to be a relative term which derives meaning by comparing the amount of Met in normal with the amount of Met in tumor cells. When there is a markedly greater difference between the amount of Met in normal than in tumor tissue, there is greater binding in the normal tissue, according to the methods of this invention. For instance, applicants have found that with regard to Met, an 80- to 150-fold or greater reduction in Met in tumor cells is considered indicative of a poor prognosis. It is well-recognized in the art that whether a prognosis is good or poor depends upon the likelihood of metastasis and survival. For instance, according to Bieche, supra, loss of met in conjunction with a certain histological grade was associated with likelihood of metastasis and hence, within 30 months a poor prognosis. Similarly, a poor prognosis is often associated with a five year survival post-surgery.

In the preferred embodiment of the present invention, a histological tumor breast biopsy section containing both normal duct tissue and adjacent tumor tissue is embedded in paraffin and blocked for about 10 minutes using a commercially available immunostaining blocking reagent. A primary antibody is then incubated with the tissue. The preferred primary antibody is selected from the group consisting of C28 (rabbit anti-human Met), C200 (rabbit antibody against the extracellular domain of the Met peptide), SP260 (rabbit anti-mouse Met), 4G10 (mouse monoclonal antibody to phosphorylated tyrosine (P-Tyr) and the 19S monoclonal (previously described in U.S. patent application Ser. No. 07/457,556). The tissue is then further incubated with a secondary antibody coupled to a fluorochrome. The secondary antibody may be donkey anti-rabbit coupled to phycoerythrin or donkey anti-mouse coupled to fluorescein isothiocyanate. Any antibody which binds to the primary antibody is a suitable secondary antibody. Antibody binding is determined by examining the fluorochrome labeled cells with a conventional light or confocal laser scanning microscope, such as the Zeiss laser scan microscope. The fluorescent intensity is then quantitated using methods known in the art. In the preferred embodiment, the relative fluorescence intensity (the intensity of the normal compared with tumor tissue) is quantitated with an Indec Laser Scan Microscope Image Processor Option. Optionally, photographs may be taken to document visualized tissue. A poor prognosis is indicated when an 80–150-fold reduction in Met in the tumor tissue relative to normal tissue is observed.

In yet another embodiment of the present invention, the abundance of met mRNA or met DNA in a breast tissue sample containing normal and tumor cells may be detected by in situ hybridization using met sequence specific probes, or by hybridization of met sequence specific probes to mRNA or DNA from normal and tumor tissue. Probe complementary to met are prepared by methods known in the art and allowed to hybridize to mRNA or DNA within a section of a tissue sample (either embedded by standard techniques, e.g. paraffin, or otherwise preserved). Unhybridized probe is removed by nuclease. Hybridization can be detected by autoradiography or other methods. The intensity of hybridization reflects the amount of met within the cells of the tissue. The observation of tumor tissue containing reduced levels of met relative to levels in the normal tissue, indicates a poor prognosis.

In yet another embodiment of the present invention, the polymerase chain reaction ("PCR") is used to detect met DNA or mRNA in a breast tissue sample. To carry out the PCR, a pair of met sequence specific primers is employed, which hybridize to opposite strands of the met gene at offset positions on the double helix. The primers provide initiation points for DNA synthesis.

In the presence of DNA polymerase, the four nucleotide triphosphates ("NTPs"), and other necessary co-factors, which are all well known to the art, new DNA strands are synthesized complementary to the templates which hybridized with the primers. Several rounds of synthesis are carried out, the double stranded products being denatured between rounds. Preferably, a thermal stable DNA polymerase is used so that it is not necessary to add enzyme anew for each round of synthesis.

The PCR produces a double stranded DNA amplification product which has the same sequence as the original stretch of the met DNA defined by the ends of the primer pair sequences. The amount of PCR product indicates the amount of met DNA or met mRNA in the sample. The product can be detected by a variety of methods well-known in the art.

Where the products are produced in a test tube, or the like, they can be resolved by agarose or polyacrylamide electrophoresis and detected by fluorescence staining, such as ethidium bromide. Alternatively, one of the NTPs may be labelled and the PCR products may be determined by measuring incorporation of the labelled NTP. A variety of other methods for resolving, detecting and measuring the amount of PCR product are well-known to the art that are suitable for use in the present invention.

In situ techniques may employ the use of fluorescent and radiolabels which can be easily quantitated by fluorescence microscopy or autoradiography, respectively. Generally, fluorescent labels will be preferred. Another labelling technique may employ enzymatic tags which generate readily quantifiable calorimetric or chemiluminescent signals.

PCR may be rendered specific for met DNA or met mRNA in in situ and in liquid PCRs. For instance, RNAse or DNAse may be used to remove one template or the other from the sample, and the use of primers that distinguish between the gene and the message (e.g. a primer that hybridizes to a sequence in the untranscribed region of the promoter will be gene specific).

In accordance with the methods of the present invention, PCR is used to detect the presence of met DNA or met mRNA in both normal and tumor breast tissue. Therefore, it is always essential to distinguish samples containing normal and tumor tissue. Reduced amounts of met DNA or met mRNA in tumor, relative to normal tissue, is predictive of tumor metastasis.

In another embodiment, RNA ("Northern") blotting may be used in the methods of the invention. According to this method, RNA is isolated from tumor and normal breast tissue by any of a number of standard procedures. (Lehrach, H., *Biochemistry,* 16: 4743 (1975)) Again, it is important that separate assays be run on the tumor and normal breast tissue so that respective hybridization results can be compared. RNA is subjected to denaturing gel electrophoresis and transferred to nitrocellulose or other support matrix. The met mRNA can be detected by hybridization of radioactively or non-radioactively labelled met. The presence of met mRNA is detected by the intensity of hybridization. The intensity observed in normal tissue is compared with that in tumor tissue; a reduced amount of intensity in tumor tissue is indicative of poor prognosis.

Other techniques suitable to the claimed methods are readily apparent to the skilled artisan and include Nuclease Protection Assays, ELISA and Western blotting, as described in Example 1.

Although the present invention is exemplified with a method of predicting the progression of breast cancer, the claimed methods are likewise applicable to predicting the progression of any tumor associated with lumen or duct-forming epithelial tissues, such as those found in the gastrointestinal tract, kidney and lung.

Although the method of the present invention involves the detection of met DNA, met mRNA or Met protein, the detection and comparison of HGF/SF DNA, mRNA or protein in normal and tumor tissue is likewise predictive of tumor progression, in accordance with the teachings of the present application.

Unless defined otherwise, all technical and scientific terms used herein have the same meaning as commonly understood by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well known to one of ordinary skill in the art. The materials, methods and examples are illustrative only and not limiting.

EXAMPLE 1

Expression of Met in Cells and Tissues of Both Human and Mouse Origin

Immunoprecipitation and Western analyses showed that met is expressed in human breast carcinoma cell line T47D (I. Keydar et al., *Eur. J. Cancer* 15: 659 (1979)) Applicants examined the distribution of Met in T47D cells by immunofluorescence and confocal laser scanning microscopy, using antibody C28 (M. Gonzatti-Haces et al., *Proc. Natl. Acad. Sci. USA* 85: 21 (1988)) or C200 rabbit antibodies directed against a C-terminal or an N-terminal peptide of Met, respectively, as shown in FIG. 1. Controls were prepared with the C28 antiserum in the presence of competing peptide or without the C28 antiserum.

T47D cells in suspension form lumen-like structures resembling mammary ducts (I. Keydar et al., *Eur. J. Cancer* 15: 659 (1979)). Analyses of T47D cells in paraffin sections stained with C28 antibody showed intense fluorescent staining in cells bordering lumen-like structures, as shown in FIG. 1A. A marked decrease in intensity was observed when competing C28 peptide was added to the primary antibody or when the primary antibody was omitted. Moreover, T47D cells stained with the C200 antibody, directed against the met extracellular domain, also showed intense fluorescent staining in cells bordering the lumen-like structures, as shown in FIG. 1A. By CLSM, applicants observed an 80-fold greater fluorescence in cells forming the lumen border than in adjacent cells, as shown in FIG. 1B.

Applicants further investigated the subcellular localization of Met by electron microscopy using indirect immunogold labeling and the C28 Met antibody. Through this analysis, applicants discovered that Met was localized to microvilli that protrude into lumen, as shown in FIG. 1C.

Figure 2:
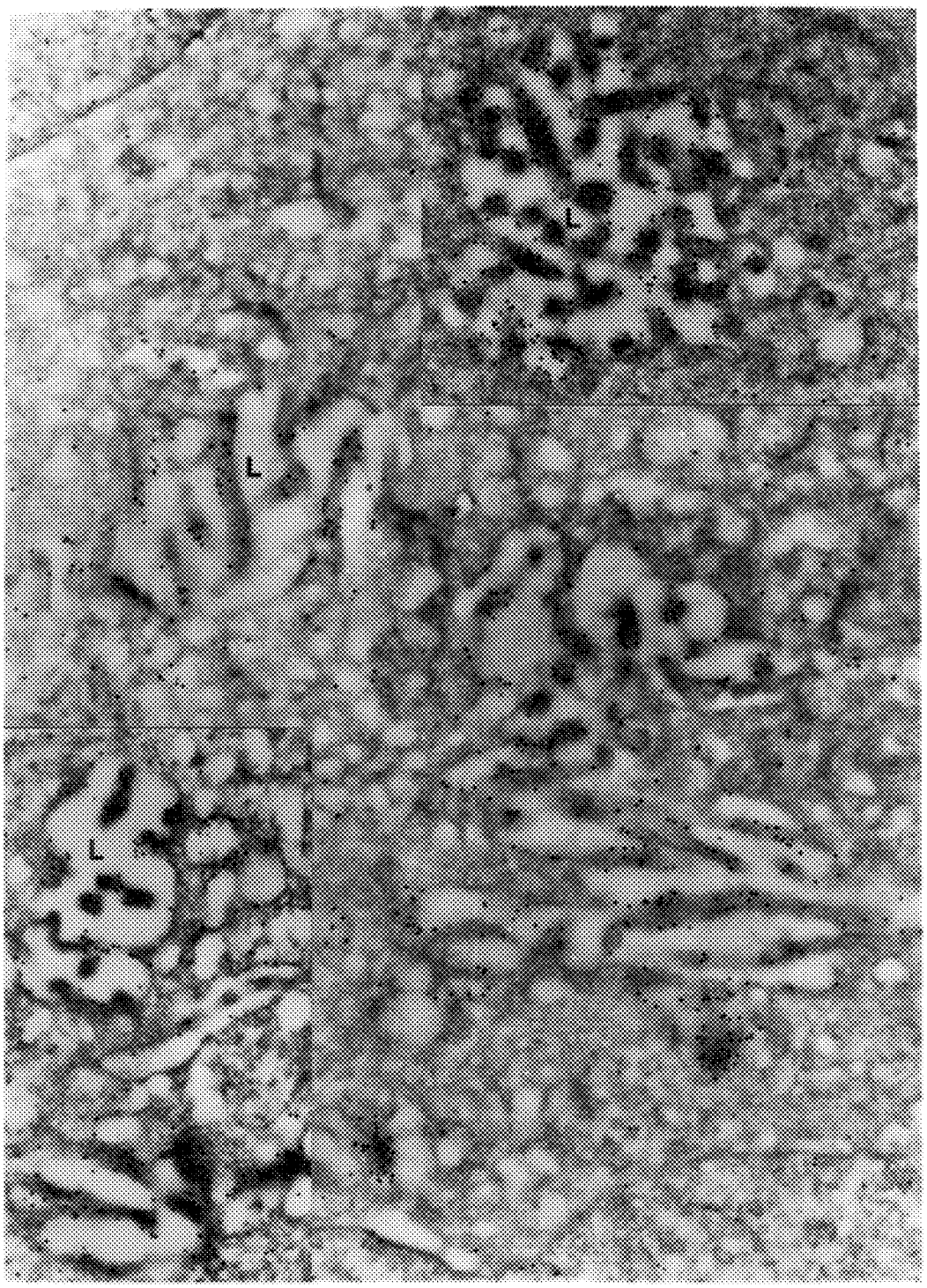
FIG. 2 shows Subcellular localization of Met in T47D cells. Immunoelectron microscopy was performed using secondary antibody labeled with 10-nm colloidal gold particles (magnification 30,000×) (For postembedding immunoelectron microscopy, fixed cells were embedded in L.R. gold resin (Electron Microscopy Science) at −25° C., sectioned with an LKB Nova Ultratome, and picked up with Formvar-coated 200 mesh gold grids. The grids were washed three times in PBS 10 minutes and incubated in 1% BSA (in PBS) for 2 hours and in rabbit anti-human C28 Met antibody (diluted 1:50 in 1% BSA) at room temperature for 1 hour. Controls were incubated either in the presence of C28 competing peptide or in the absence of the primary antibody. The grids were washed again in PBS, incubated in RPM11640 medium for 20 minutes in 1% BSA as above, and reacted with goat anti-rabbit IgG gold (10-nm diameter; 1:10 diluted in 1% BSA; Amersham) at room temperature for 1 hour. The grids were finally washed in PBS and distilled water and stained with uranyl acetate and lead citrate. The sections were observed and photographed using a Philips EM 410 electron microscope.). Met is localized in microvilli that protrude into lumen (L) and could account for the apical staining observed in cells bordering the lumen (A and B).
Figure 5A:
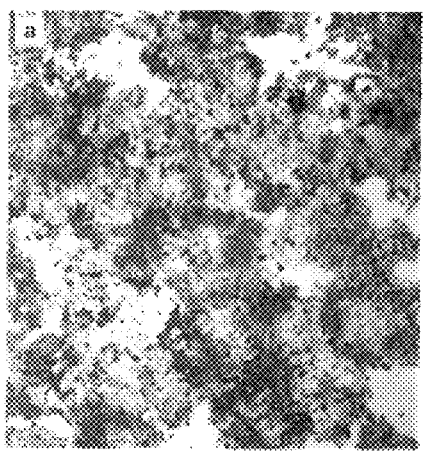
FIGS. 5A–F relates to HGF/SF induction of lumen formation in SW480 and HT29 human colon carcinoma cell lines. The cells were treated with the specified concentration of HGF/SF when they were −70% confluent. Magnification is ×164.
Figure 5D:
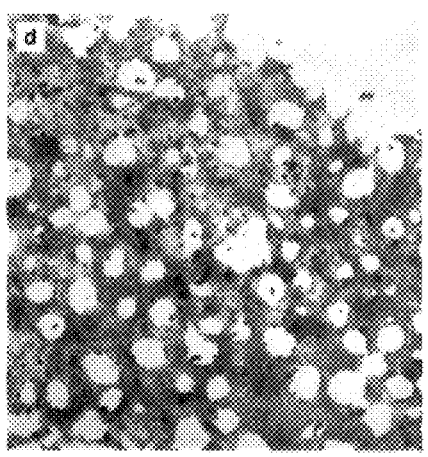
Figure 5B:
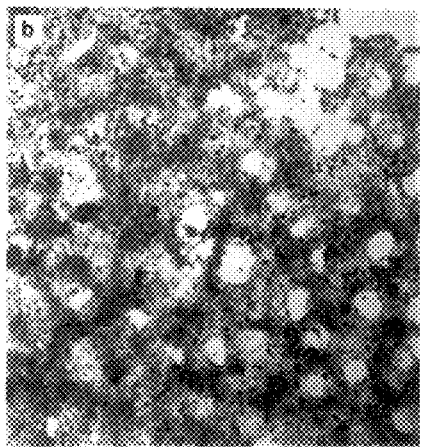
Figure 5E:
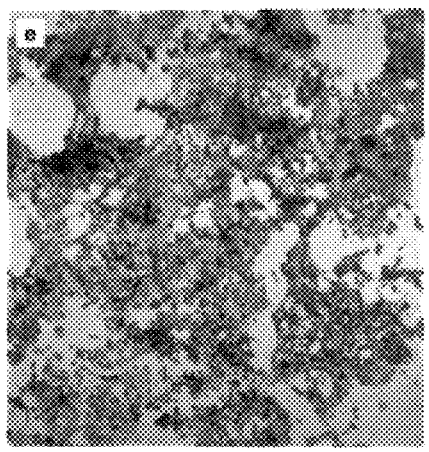
Figure 5C:
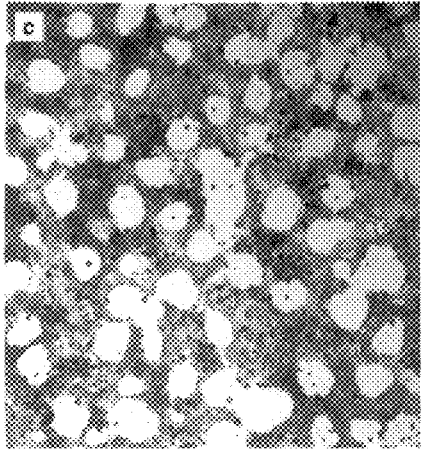
Figure 5F:
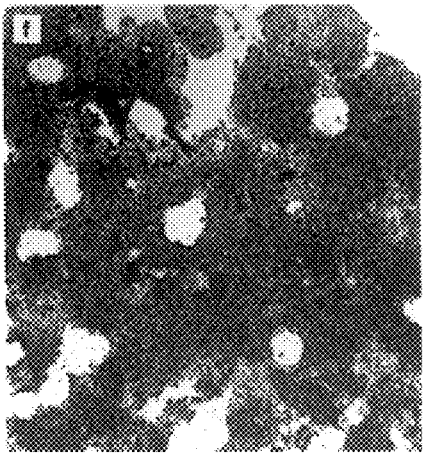
Figure 6:
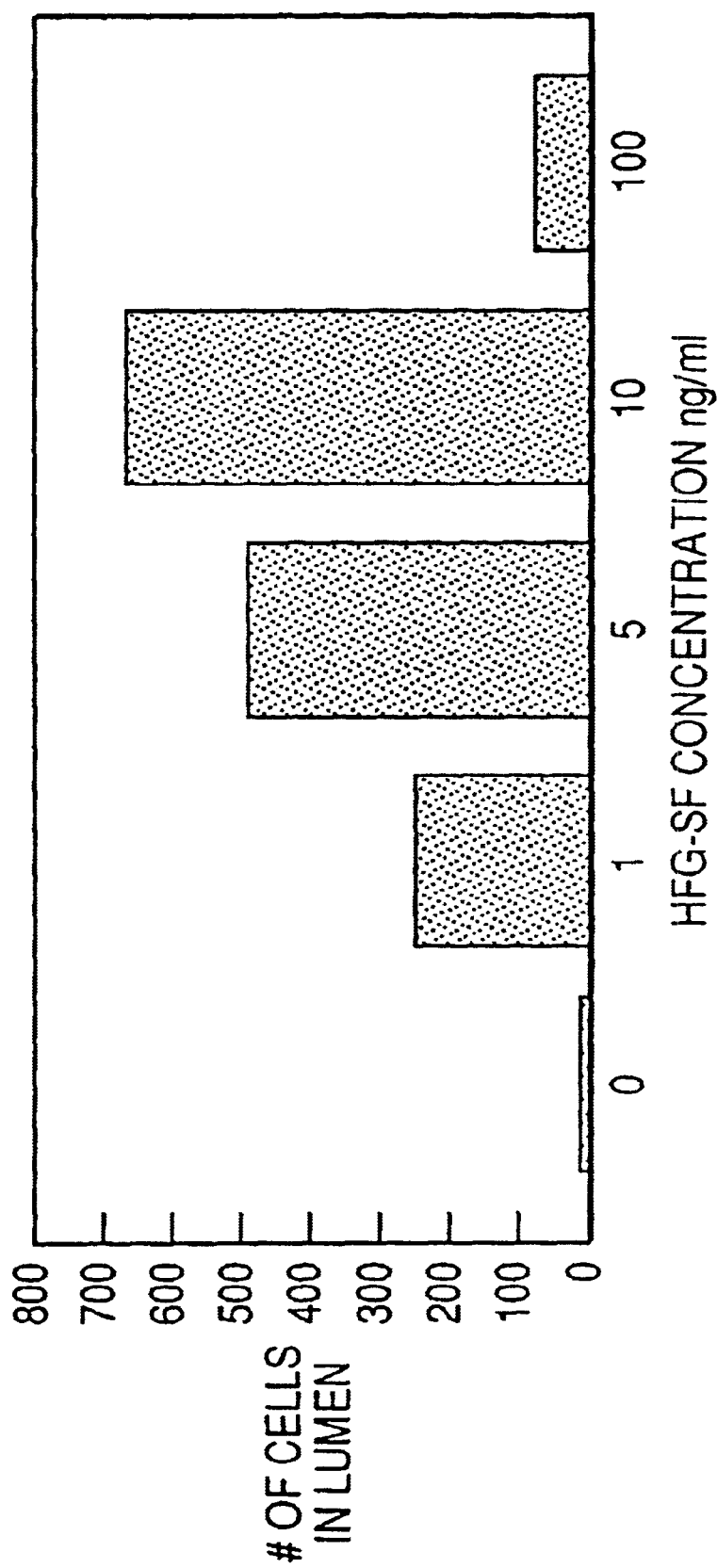
FIG. 6 shows the influence of HGF/SF concentration on lumen formation. The number of cells forming lumen structures was calculated for each HGF/SF concentration.

The intense Met-specific staining of cells lining the lumen borders in T47D breast carcinoma cells led applicants to examine met expression in normal and abnormal human breast tissue. Specifically, applicants examined fifty human breast carcinoma biopsies by CLSM using the C28 Met antibody. The normal and tumor tissue from a representative breast biopsy is shown in FIG. 2. Applicants observed intense Met fluorescence in cells that form a normal mammary duct, as shown in FIG. 2A. The intensity of staining was 80-fold greater in the duct-forming cells than in the adjacent nonductal cells. The pattern of Met staining in the mammary duct was similar to, but higher than, that observed in the T47D lumen-like structures. Applicants further discovered that, in contrast, Met staining in adjacent breast tumor tissue was always reduced, but even in the disrupted architecture of the tumor, Met fluorescence was evident in lumen- or duct-like structures, as shown in FIG. 2C.

Met is rapidly phosphorylated in tyrosine residues after HGF/SF activation (D. P. Bottaro et al., *Science* 251: 802 (1991); L. Naldini et al., *Oncogene* 6: 501 (1991)). Applicants have further observed that anti-phosphotyrosine (anti-P-Tyr) monoclonal antibody labeling colocalizes with Met staining in cells activated with the met ligand, HGF/SF. In light of this, applicants costained breast tissue samples with the anti-P-Tyr antibody and found intense anti-P-Tyr fluorescence that colocalized with Met staining in the cells forming normal breast ducts (FIG. 2B). Applicants conclude from these results that Met and its substrates are activated in the cells bordering the normal breast duct. As with the lower Met staining of tumor tissue (FIG. 2C), applicants also observed reduced levels of anti-P-Tyr staining in the tumor cells (FIG. 2D); however, even the lower levels of anti-P-Tyr fluorescence colocalized with Met staining.

Thus, applicants have observed that human met expression both in vitro and in vivo is concentrated in cells bordering lumen-like structures. Since extensive lumen and duct formation occurs in the early development of the digestive tract, applicants further investigated met expression in this tissue in mouse embryos. These analyses, performed using a C-terminal rabbit peptide antibody, SP260 (A. Iyer et al., Cell Growth & Diff. 1: 87 (1990)), showed that in 11-day-old mouse embryos, met is expressed in the lumen-bordering cells, as shown in FIG. 3. Applicants noted that, as in human samples, intense Met staining was evident on the apical side of the cells forming the lumen of the digestive tract, as shown in FIGS. 3A and 3D, and was 50-fold higher in these cells than in the surrounding tissue. Serial sections stained in the absence of the primary C-terminal mouse Met antibody or in the presence of competing peptide showed much lower levels of fluorescence, as shown in FIGS. 3B and 3C. Moreover, as in the cells lining the human breast duct, mouse Met staining colocalized with anti-P-Tyr staining in the lining of the embryonic digestive tract, as shown in FIG. 3E. Thus, applicants have discovered that the Met receptor appears to be preferentially expressed in the border cells of the breast duct and the gastrointestinal tract lumen. Similarly, Met staining in lumen-like structures has been observed in human gastrointestinal lumen and lumen of biliary ducts and esophagus (M. Pratt et al. Int. J. Cancer 49: 323 (1991)). The colocalization of Met staining with anti-P-Tyr immunofluorescence implies that the Met receptor is activated in the lumen-forming cells of the breast duct and gastrointestinal tract, a shown in FIGS. 2 and 3.

Having established a correlation between the expression of Met and lumen formation, applicants tested whether Met-HGF/SF could induce lumen formation in human epithelial carcinoma cells in vitro. Specifically, cells expressing Met were exposed to varying concentrations of HGF/SF (1–100 ng/ml). More specifically, cells were grown on 16-chamber Labtek slides (Nunc) and treated with specific concentrations of HGF/SF (95% pure, Collaborative Research) for 24 hours. After two washes in PBS, cells were fixed for 10 minutes in cold methanol (−20° C.) and washed extensively with PBS. Cells were also stained for 10 minutes with 0.1% methylene blue in PBS and were visualized and photographed using a Zeiss microscope. The results with two human colon carcinoma cell lines, SW480 and HT29, are shown in FIG. 4. Indeed, applicants observed dramatic formation of lumen structures in these cells (as well as in breast carcinoma cell lines) when the cells were grown on glass (70% confluent) and treated with HGF/SF. Lumen formation was cell density dependent and not obvious when cells were grown in plastic tissue culture flasks or treated with epidermal growth factor instead of HGF/SF under the same conditions. Furthermore, lumen formation was dependent on the dose of HGF/SF, as shown in FIGS. 4A and 4B. Thus, when cells were treated with 1–10 ng of HGF/SF per milliliter of medium, applicants observed lumen-like structures with a uniform size. The regularity in the size indicates that the number of cells forming the lumen border is controlled and that cell-cell interactions play an important role in this formation.

EXAMPLE 2

Immunofluorescence Assays

For immunofluorescence assays, fixed cells or paraffin-embedded tissues, cells, and embryo sections (I. Keydar et al., Eur. J. Cancer 15: 659 (1979)) were blocked for 10 minutes using the Biomeda immunostaining kit blocking reagents. Primary antibody (C28, rabbit anti-human Met at 1:100 dilution in PBS according to the methods of M. Gonzatti-Haces et al., Proc. Natl. Acad. Sci. USA 85: 21 (1988); C200, rabbit antibody prepared against the extracellular domain of the Met peptide, amino acids 643–663, according to the methods of M. Park et al., Proc. Natl. Acad. Sci. USA 84: 6379 (1987).; SP260, rabbit anti-mouse Met at a 1:100 dilution in PBS; 4G10, mouse monoclonal antibody to phosphorylated tyrosine (P-Tyr), according to D. K. Morrison et al. Cell 58: 649 (1989)) was added and incubated for 2 hours at room temperature. Secondary antibody incubation (donkey anti-rabbit coupled to phycoerythrin at 1:50 and donkey anti-mouse coupled to fluorescein isothiocyanate at 1:100 (Jackson ImmunoResearch Laboratories, Inc.) were performed for 1 hour at room temperature. After an extensive washing, cells were fixed using gel mount (Biomedia).

Fluorochrome-labeled cells were examined using a Zeiss laser scan microscope (LSM) having the following configuration: 25 nW argon a nd HeNe lasers, 488, 514, and 543 maximum lines; control Indec (Sungate) software for image acquisition of X-Y scan, Z-series scan three-dimensional visualization. Photographs were taken using a Sony color video prin ter mavigraph and Sony UPC-5010a color print paper. When comparing the fluorescence intensity, applicants used identical parameters for each image (e.g., scanning line, laser light, contrast brightness) and assessed quantitation of the relative fluorescence by using an Indec LSM Image Processor Option, "Histogram."

EXAMPLE 3

Immunoelectron Microscopy

For postembedding immunoelectron microscopy, fixed cells were embedded in L.R. gold resin (Electron Microscopy Science) at −25° C., sectioned with an LKB Nova Ultratome, and picked up with Formvar-coated 200 mesh gold grids. The grids were washed three times in PBS 10 min and incubated in 1% BSA (in PBS) for 2 hours and in rabbin anti-human C28 Met antibody (diluted 1:50 in 1% BSA) at room temperature for 1 hour. Controls were incubated either in the presence of C28 competing peptide or in the absence of the primary antibody. The grids were washed again in PBS, incubated in RPM 11640 medium for 20 min in 1% BSA as above, and reacted with goat anti-rabbit IgG gold (10-nm diameter; 1:10 diluted in 1% BSA; Amersham) at room temperature for 1 hour. The grids were finally washed in PBS and distilled water and stained with uranyl acetate and lead citrate. The sections were observed and photographed using a Philips EM 410 electron microscope.

What is claimed is:

1. A method for predicting the progression of a breast cancer comprising the steps of:

(a) determining one or more of met DNA abundance, met mRNA abundance, or Met protein abundance in normal breast tissue and in tumor breast tissue and (b) com paring the abundance of said met DNA, met RNA or Met protein in normal breast tissue with said met DNA, met RNA or Met protein in tumor breast tissue, wherein said normal and tumor tissue is from the same breast, and wherein a higher abundance of met DNA, met RNA, or Met protein in said normal tissue than in said tumor tissue indicates a poor prognosis.

2. A method for predicting the progression of a breast cancer by determining Met protein abundance in normal breast tissue and in tumor breast tissue, comprising the steps of:

a) contacting a section from a breast tumor with an antibody reagent specific for Met protein under antibody binding conditions, wherein said section contains normal breast tissue and tumor tissue;

b) determining the binding of the reagent to Met protein in said normal tissue and said tumor tissue; and c) comparing said binding of said reagent to Met protein in said normal tissue with said binding in said tumor tissue; wherein, greater binding of said reagent to said normal than to said tumor tissue indicates a poor prognosis.

3. The method according to claim 2, wherein said antibody reagent is an immunofluorescent stain comprising an antibody selected from the group consisting of the C28, C200, 19S, SP260 and 4G10 monoclonal antibodies.

4. The method according to claim 2, wherein said normal breast tissue is breast duct tissue.

* * * * *